United States Patent [19]

Allison et al.

[11] Patent Number: 5,370,628
[45] Date of Patent: Dec. 6, 1994

[54] SAFETY NEEDLE AND SYRINGE

[76] Inventors: Alan C. Allison, 233 Marvilla Cir., Pacifica, Calif. 94044; Richard A. Jaffe, 786 Wildwood Ave., Palo Alto, Calif. 94303

[21] Appl. No.: 128,868

[22] Filed: Sep. 29, 1993

Related U.S. Application Data

[63] Continuation-in-part of Ser. No. 738,419, Jul. 31, 1991, Pat. No. 5,151,088.

[51] Int. Cl.5 .................................................. A61M 5/32
[52] U.S. Cl. ..................................... 604/192; 604/198; 604/263
[58] Field of Search ............... 604/187, 192, 198, 218, 604/263

[56] References Cited

U.S. PATENT DOCUMENTS

| | | | |
|---|---|---|---|
| 4,737,150 | 4/1988 | Baeumle et al. | 604/198 |
| 4,863,434 | 9/1989 | Bayless | 604/198 |
| 5,151,088 | 9/1992 | Allison et al. | 604/192 |

*Primary Examiner*—John D. Yasko
*Attorney, Agent, or Firm*—Ostrager, Chong & Flaherty

[57] ABSTRACT

A disposable safety needle and syringe assembly includes a needle shield movably positioned within a syringe housing. Movement of the needle shield from the housing is effected by movement of the syringe plunger and plunger piston following completion of an injection whereby the needle shield envelopes the needle extending from the housing to prevent accidental needle sticks. The plunger piston is disengagable from the plunger at a limit of travel upon retraction of the plunger, thus maintaining the shield in a locked position enveloping the needle. The syringe and needle assembly can then be safely handled for disposal, and the possibility of inadvertent reuse of the needle is eliminated.

14 Claims, 10 Drawing Sheets

SAFETY NEEDLE AND SYRINGE

This patent application is a continuation-in-part of U.S. application No. 738,419, filed Jul. 31, 1991, by A. Christopher Allison and Richard A. Jaffe, now issued as U.S. Pat. No. 5,151,088, as of Sep. 29, 1992.

BACKGROUND OF THE INVENTION

This invention relates generally to hypodermic needles and syringes, and more particularly the invention relates to a disposable syringe and safety needle assembly.

The safe use and disposal of hypodermic needles and syringes are a concern in the medical and health professions. Needle stick injuries following use of a needle pose a risk to both patient and user, and especially with present risk of HIV and HBV infection care must be taken in the safe handling and disposal of used needles and syringes. A safety cover for the used needle is a recognized requirement.

A number of safety syringe designs incorporating needle covers have been proposed. U.S. Pat. No. 4,909,791 and No. 4,982,842 employ jaw members pivotally mounted on a syringe barrel for covering a needle after use.

U.S. Pat. No. 4,883,471 and No. 4,935,014 disclose syringe assemblies in which the needle is drawn into the syringe after use.

U.S. Pat. No. 4,969,877 discloses a syringe assembly in which an outer casing is provided around an inner chamber or syringe portion which slides in the outer casing to an operational position and to a retracted position at the forward and rearward ends of the outer casing, respectively.

U.S. Pat. No. 4,874,382 incorporates a protective shield within the body of a syringe into which a needle is drawn after use. A spring biasing mechanism is required in drawing the needle into the sheath.

U.S. Pat. No. 4,863,435 incorporates an outer shield which is spring biased to slide on the syringe to cover a needle after use and which is retractable on the syringe to permit needle injections.

While each of these safety syringes provides some protection against accidental needle injury, the designs require a relatively complex mechanism, are bulky in handling and use, and expensive to manufacture. Moreover, actuation of the safety features can require use of both hands of the user.

The present invention is directed to an improved safety needle and syringe assembly which overcomes limitations of the prior art.

SUMMARY OF THE INVENTION

Accordingly, an object of the invention is an improved safety needle and syringe assembly.

Another object of the invention is a safety needle and syringe assembly which is simple in design and readily manufacturable.

Still another object of the invention is a safety needle and design in which the user's hand remains behind the needle at all times during and after use without changing finger position used during an injection.

A feature of the invention is an integral shield positioned within a syringe housing and which is moved to cover the needle following an injection by the plunger within the syringe housing.

Briefly, a disposable syringe and needle assembly in accordance with the invention is conventional in appearance and handling. A small rigid retractable needle shield is provided in the syringe, and following an injection the needle shield can be easily and quickly extended to a locked position covering the needle. Extension of the shield to the locked position is accomplished by pressing the syringe plunger pass the zero volume point into engagement with the needle shield which is then pushed from one end of the syringe housing until it locks at the end of the syringe barrel. The syringe and needle assembly can then be safely handled for disposal. Further, the possibility of inadvertent reuse of the needle is eliminated due to the covered needle.

In a preferred embodiment, the needle includes an inner portion within the syringe housing which extends through a forward seal around one end of the shield. The plunger includes a central bore having an axial length to accommodate the inner portion of the needle. Following an injection, the piston of the plunger engages the end of the inner portion of the needle and the forward seal. As the piston pushes the forward seal and shield toward the end of the housing, the inner portion of the needle is received in the axial bore of the plunger. Thus, actuation of the shield is effected by the same one hand operation as the injection by further movement of the plunger and piston.

In a preferred embodiment, the needle support has spaced lugs or ribs which engage the inner wall of the syringe housing. The needle shield is segmented with shield segments passing between the support ribs during extension of the shield.

The present invention is particularly directed to an improvement for locking the shield in positions on the syringe, and for a plunger.

DETAILED DESCRIPTION OF ILLUSTRATIVE EMBODIMENTS

Figure 1A:
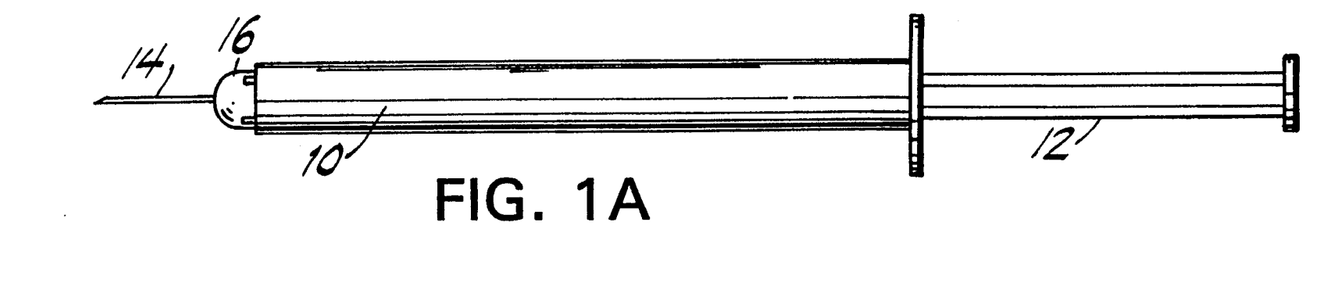
FIGS. 1A-1C are side views of a needle and syringe assembly in accordance with one embodiment of the invention before use and after use, respectively.
Figure 1B:
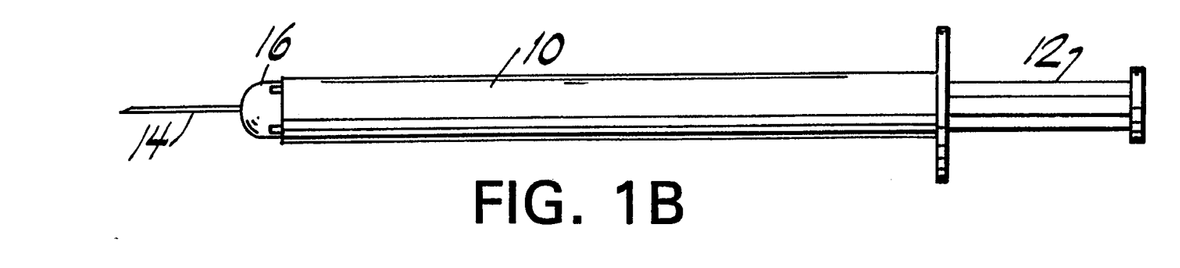
Figure 1C:
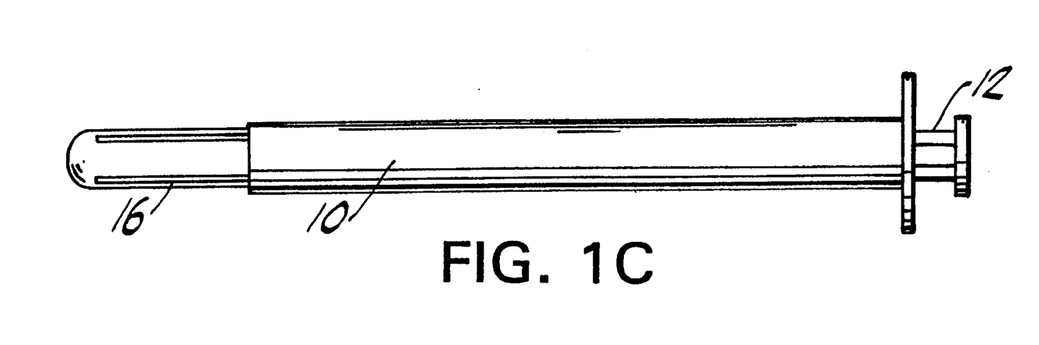

Referring now to the drawing, FIG. 1A–1C are side views of a needle and syringe assembly in accordance with one embodiment of the invention prior to injection, after injection, and after engaging a needle shield. The assembly includes a syringe 10, a plunger 12, a needle 14 extending from one end of the syringe 10 and a shield 16 positionable about the needle 14 and extending from the one end of the syringe 10 from which the needle 14 extends.

The user inserts the needle into a patient and injects the contents thereof by pushing plunger 12 as shown in FIG. 1B. The needle can then be removed from the patient while the plunger 12 is pushed further into the syringe 10 thereby pushing the needle shield 16 from the syringe and covering the needle. The syringe and needle assembly can then be safely handled for disposal. Further, with a covered needle the possibility of inadvertent reuse of the needle is also eliminated.

An important feature of the needle and syringe assembly in accordance with the invention is that the use and appearance thereof are almost unaffected by inclusion of the needle shield. Further, needle protection can be accomplished without changing finger positions used during injection with an easy one-handed operation. Importantly, as will be described further hereinbelow, the needle and syringe assembly requires few parts which translates to low production cost.

Figure 2:
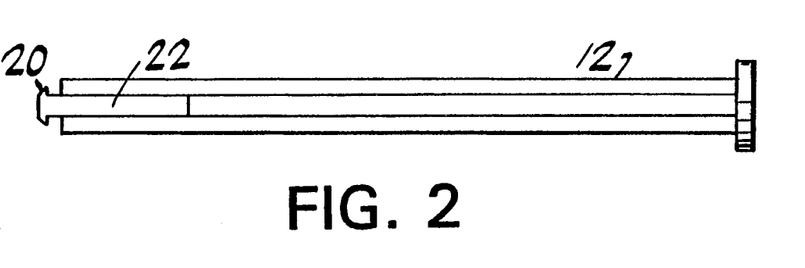
FIG. 2 is a side view of the plunger seen as used in the assembly of FIG. 1.
Figure 3A:
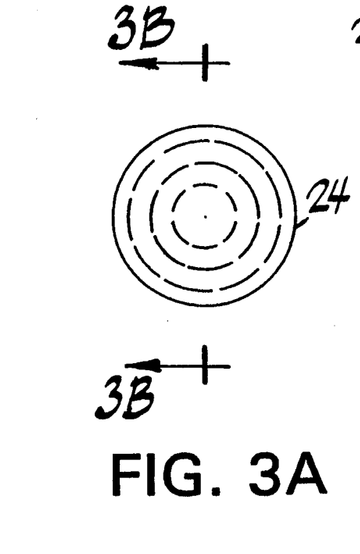
FIGS. 3A and 3B are end and side views of the plunger piston in the syringe of FIG. 1.
Figure 3B:
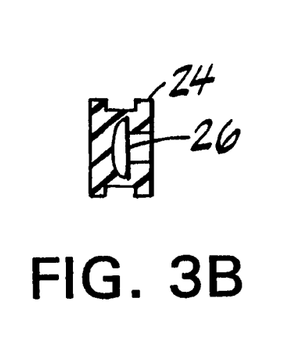

FIG. 2 is an exploded side view of the plunger and the plunger piston used in the syringe of FIG. 1. The plunger 12 includes an extension 20 with a central bore 22 extending through the extension into the plunger 12. The central bore receives an inner portion of the needle as will be described hereinbelow. The extension 20 includes a disk shaped head which is received in an opening in the pliable plunger piston shown in FIGS. 3A, 3B. The plunger piston, 24 is a disk shaped body as illustrated in the end view of FIG. 3A which has a cavity 26 in one side thereof for receiving the disk shaped head of extension 20 of plunger stem 12. The piston can be made of a pliable rubber, for example.

Figure 4A:
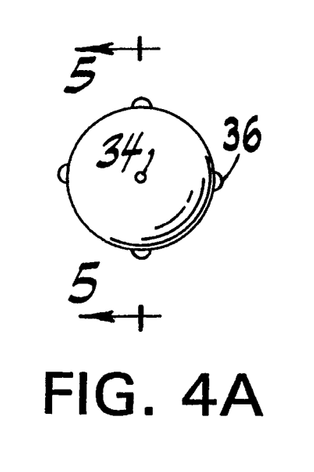
FIGS. 4A and 4B are an end view and side view of the needle shield in the syringe of FIG. 1.
Figure 4B:
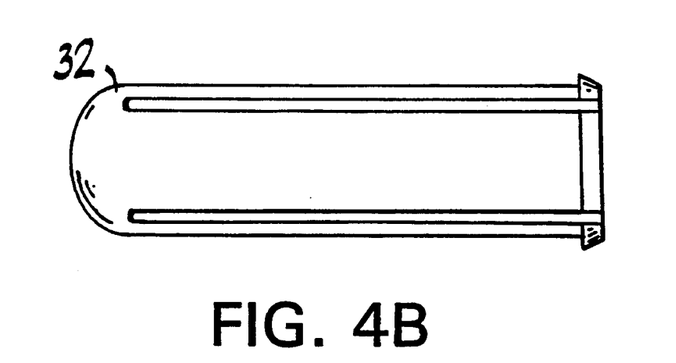
Figure 5:
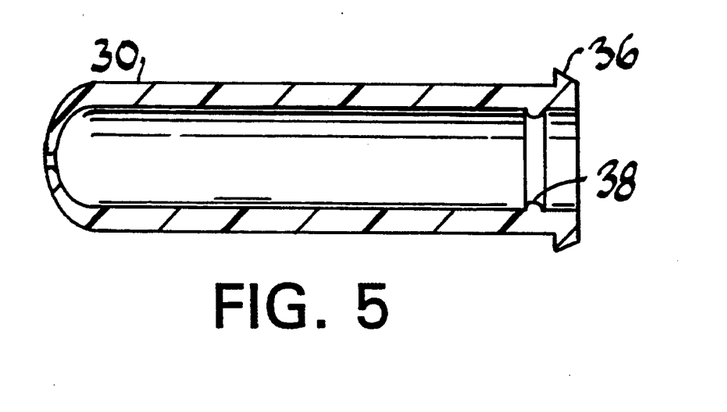
FIG. 5 is a section view of the needle shield taken along the line 5—5 in FIG. 4A.

FIGS. 4A and 4B are an end view and a side view, respectively, of the needle shield which may comprise a hard plastic material. The shield includes a plurality of segmented portions 30 which support a generally hemispherical and portion 32 having a hole 34 therein for receiving the needle. FIG. 5 is a section view of the needle shield taken along the line 5—5 of FIG. 4A. The shield has outer detents 36 and inner detents 36 on one end which serve to limit the extension of the shield from the syringe body following an injection.

Figure 6A:
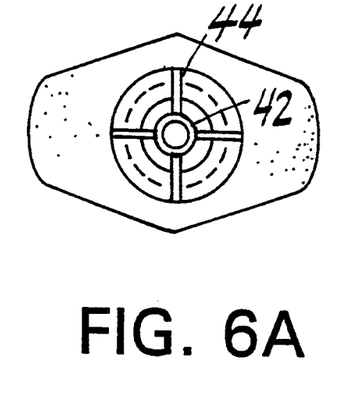
FIGS. 6A and 6B are an end view and a side view in section of the needle support and syringe barrel, respectively.
Figure 6B:
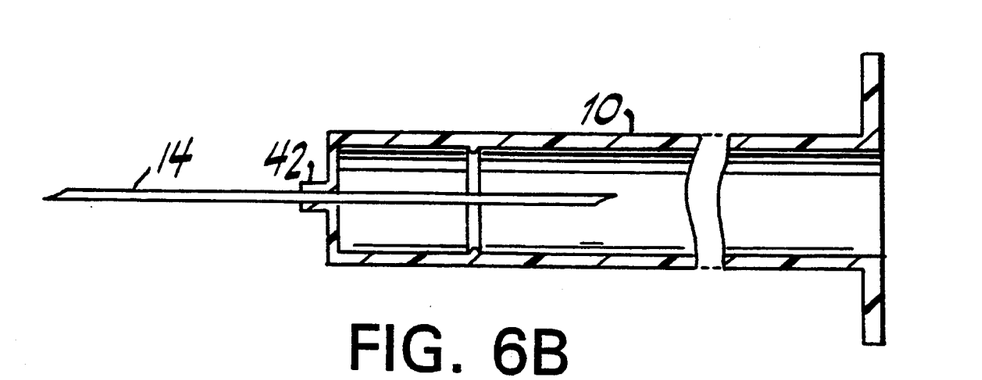
Figure 7A:
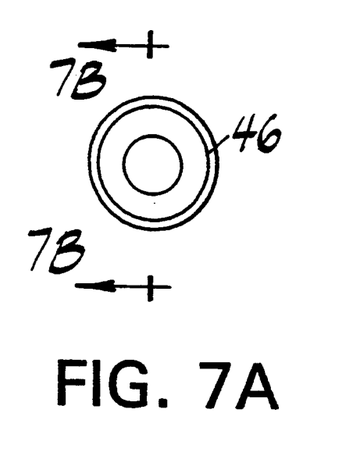
FIGS. 7A and 7B are an end view and a section view of the shield piston.
Figure 7B:
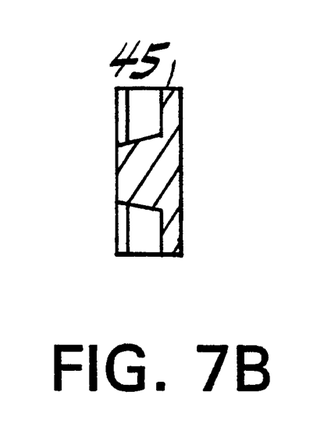

FIG. 6A and FIG. 6B are an end view and side view in section of the needle, needle holder, and syringe body. The needle 14 is mounted in a support 42 having a plurality of ribs or lugs 44 which engage the inner surface of the syringe housing 10. The needle 14 has an inner portion extending within the housing 10 and an outer portion for insertion in a patient. FIG. 7A and 7B are an end view and side view, respectively, of a shield piston used in pushing a shield from a syringe following an injection.

Figure 8A:
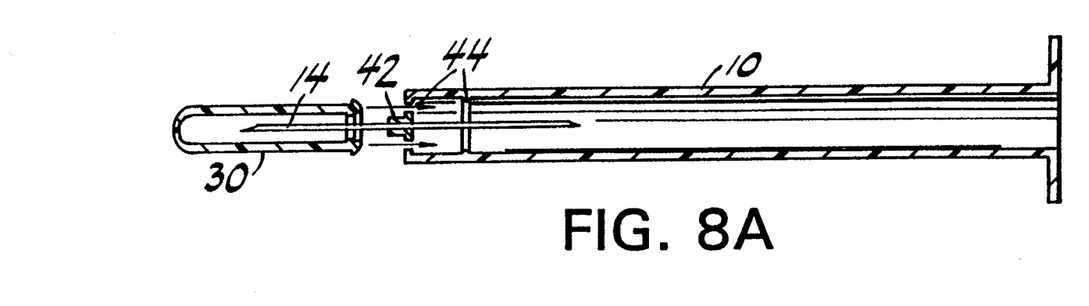
FIGS. 8A-8D are side views in section illustrating assembly of the syringe and needle assembly of FIG. 1.

Consider now FIGS. 8A–8D which are side views in section illustrating the assembly of the needle and syringe. In FIG. 8A the needle 14 and support 42 are inserted in one end of the syringe housing 10, and the shield 30 is then inserted in the housing 10 with the segments of the shield passing between the ribs of the needle support. The segments must be flexed so that the detents of the shield can pass inner detents 44 projecting from the inner surface of housing 10.

Figure 8B:
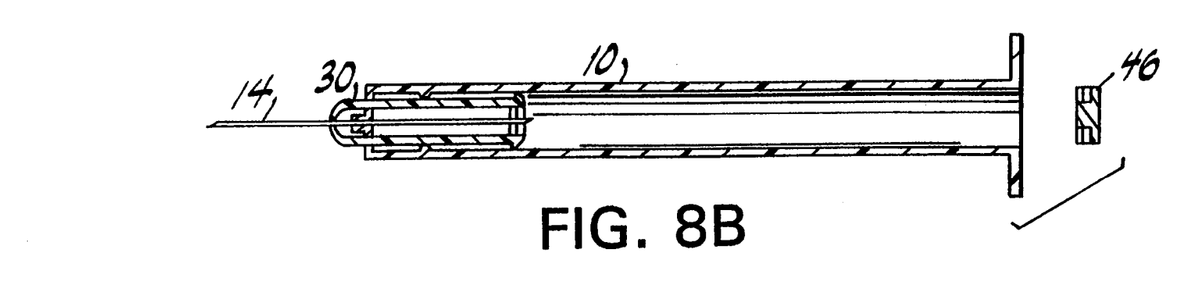
Figure 8C:
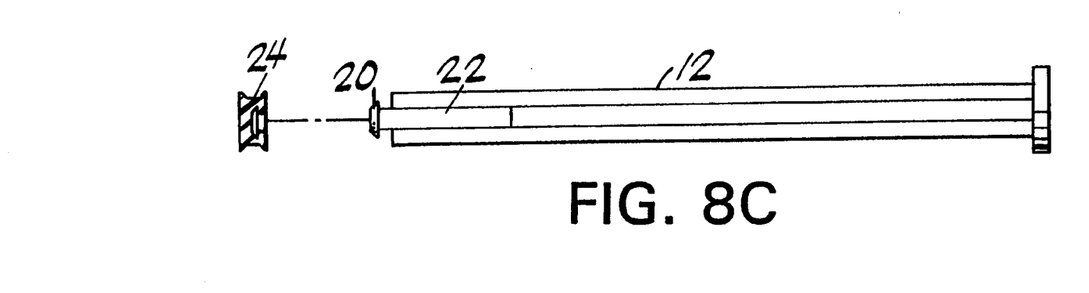
Figure 8D:
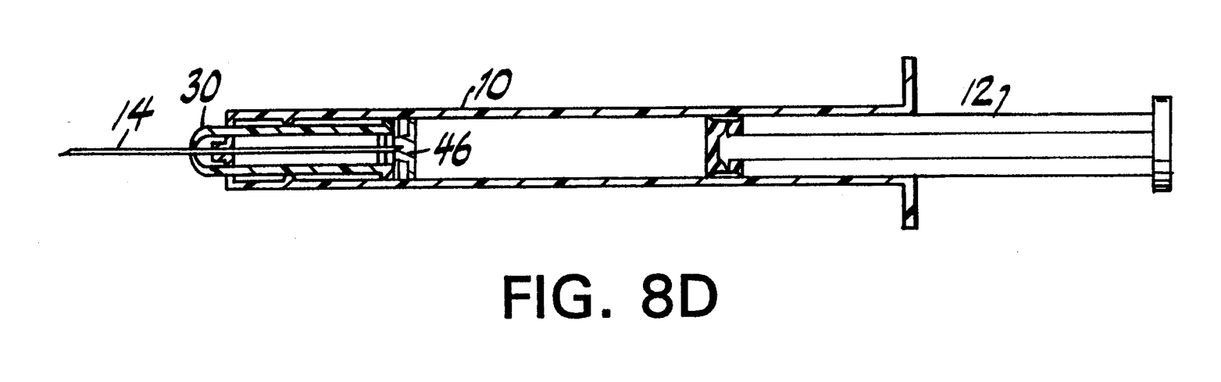

In FIG. 8B, while the shield 30 is held in place, the shield piston 46 is inserted from the opposing end of the syringe housing until the piston engages the end of the shield segments 30 and the inner end of needle 14 passes through the central portion of the piston. In FIG. 8C the plunger and piston are assembled, and the plunger assembly is then inserted into the syringe body as shown in FIG. 8D. The completed syringe is now ready for use.

Figure 9A:
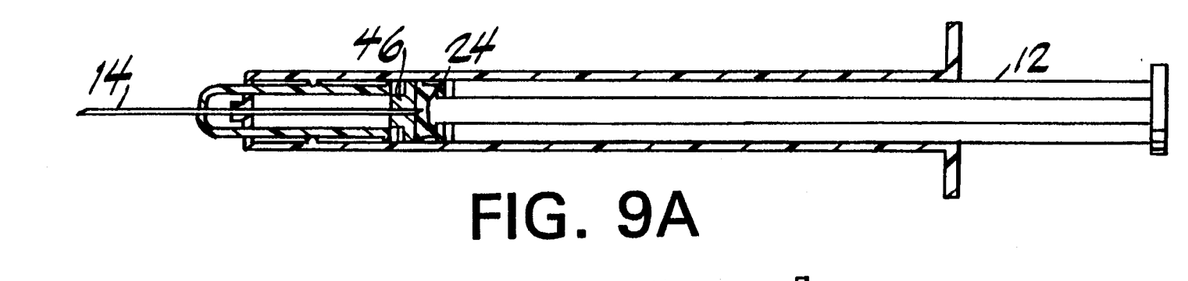
FIGS. 9A-9D are side views in section illustrating operation of the syringe and safety needle assembly of FIG. 1.

FIGS. 9A–9D are side views in section illustrating operation of the needle and syringe assembly. FIG. 9A shows the assembled syringe prior to use and as shipped from a factory. The plunger 12 is inserted in the housing to a point where the plunger piston 24 engages the shield piston 45.

Figure 9B:
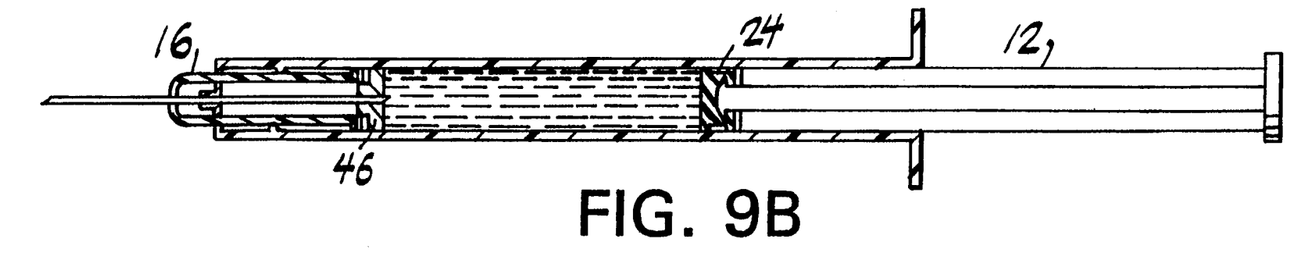
Figure 9C:
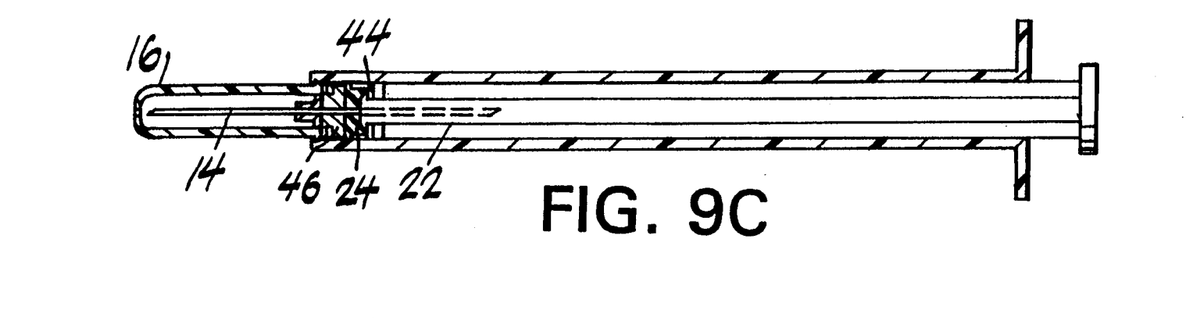

When used, liquid is drawn into the syringe as illustrated in FIG. 9B by withdrawing the plunger 12. After injection has been completed, further pressure on the plunger piston 24 moves the shield piston 46 and the shield 32 downward from one end of the syringe 10 over the needle 14 as shown in FIG. 9C. The rubber plunger piston 24 and the shield piston 46 become locked between the detents 44 on the inner surface of the syringe housing 10, and the inner portion of the needle 14 pierces the plunger and is accommodated in the central bore 22 in the plunger 12.

Figure 9D:
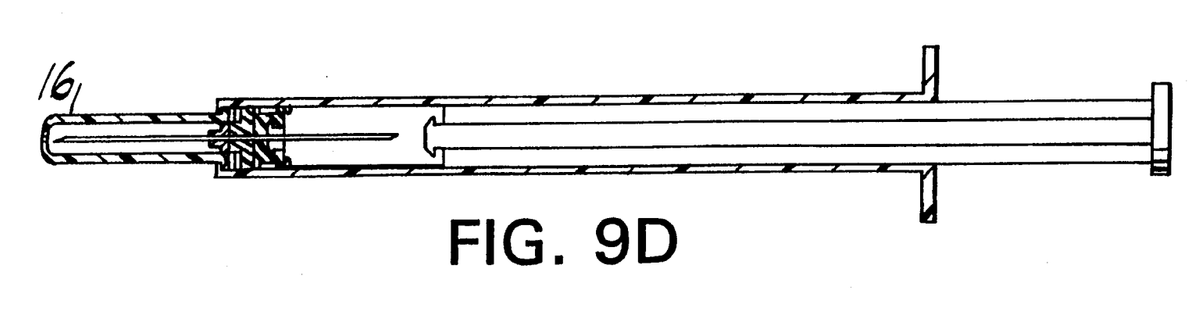
Figure 10A:
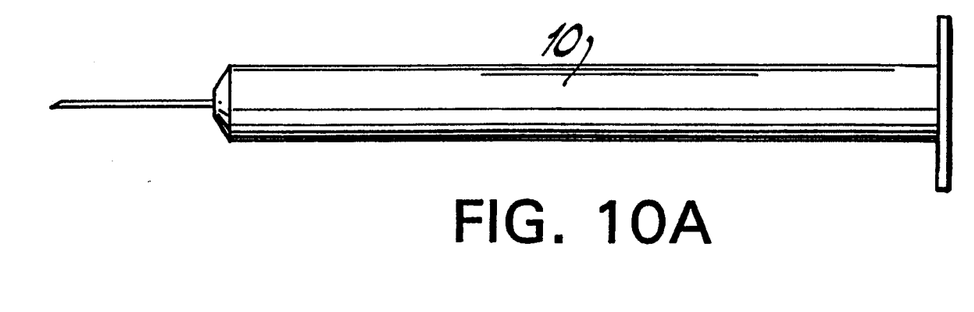
FIGS. 10A-10D illustrate an improvement in the needle shield for positive locking of the shield in positions of the syringe body.
Figure 10B:
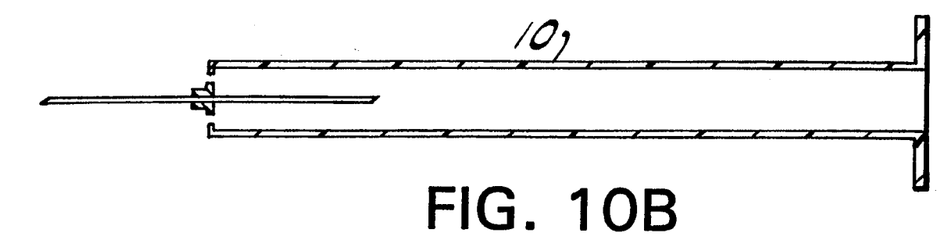
Figure 10C:
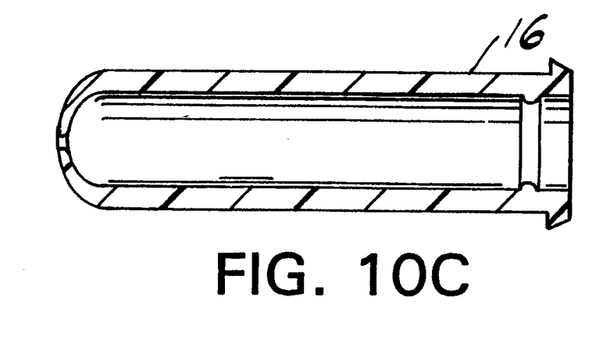
Figure 10D:
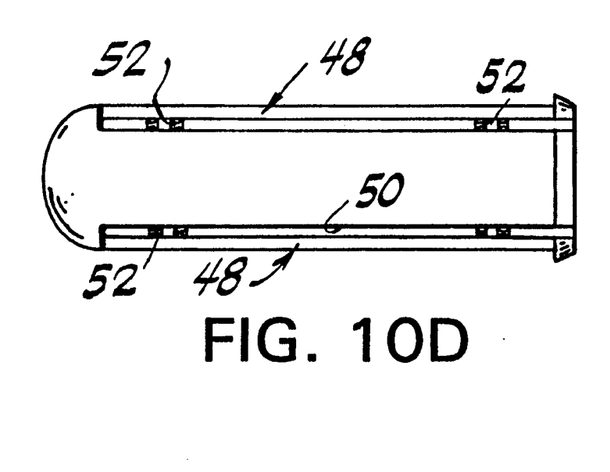

Retraction of the plunger 12 results in separation of the plunger and plunger piston while the shield 16 remains intact over the external position of needle 14. The shield 16 remains in a locked position due to the plunger piston 24 and shield piston 46 being locked between the detents 44 on the inner surface of the syringe. Thus, the needle shield is easily and quickly extended to a locked position completely covering the needle by simply pressing the syringe plunger past the zero volume point until it locks at the end of the syringe barrel.

In testing it is found that the prior to pressing the plunger past the zero volume point, the shield 16 may sometimes begin to move under the hydraulic pressure applied to the shield piston 46 during normal use of the syringe. Accordingly, the present invention is particularly directed to an improvement for positive locking of the shield 16 when it is in both the uncovered and covered positions.

Referring to FIGS. 10A–10D, the shield 16 is formed with shallow linear channels 48 for retaining and guiding the movement of the syringe body detents 44 therein. The linear channels have bottom walls 50 provided with engaging points 52 at the uncovered and covered positions for engaging the syringe body detents positively to prevent unintended displacement of the shield. At least 60% more force would be required for release of the shield from the uncovered position. Typically, 3 to 5 pounds of hydraulic pressure is exerted during injection, whereas 7 to 8 pounds of pressure would be required to release the shield from the engaging points. After injection, the engaging points provide permanent locking of the shield in the covered position. The engaging points may also be configured as slots engaging ribs on the syringe walls, or ribs engaging slots in the syringe walls.

As seen in FIG. 9A, assembly of a conventional syringe with the shield in the uncovered position will result in the plunger 12 projecting a given length from the end of the syringe body 10. This may present a problem that the plunger will be accidentally pushed inwardly and advance the shield 16 over the needle 14 so that it cannot be properly used for injection. The present invention therefore provides a further improvement which positions the plunger flush with the syringe guard when not in use, and allows the plunger to be extended to its full length for injection use.

Figures 11A, 11C:
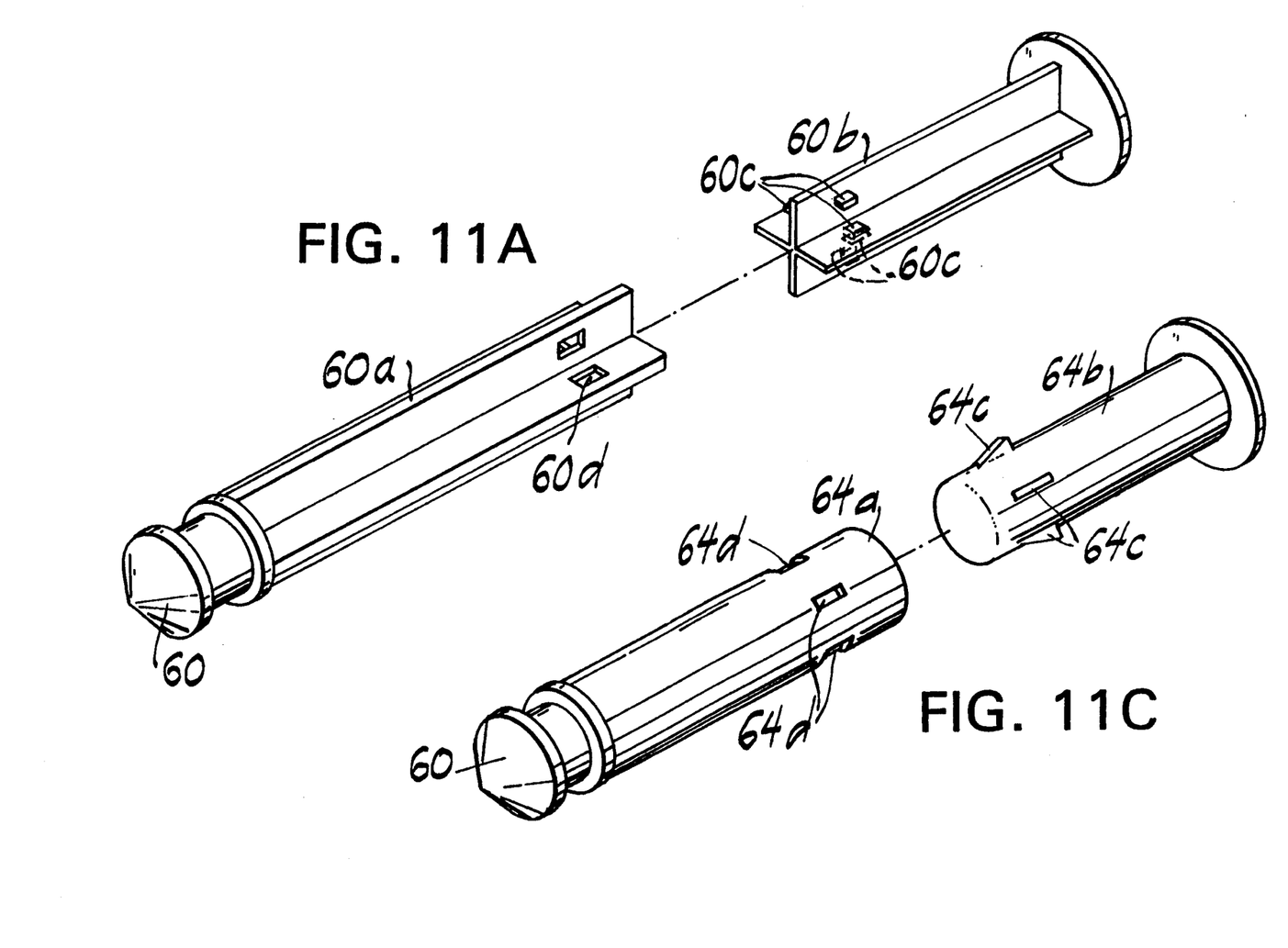
FIGS. 11A-11D illustrate an improvement in the plunger for allowing the plunger to be telescoped to a shortened length and extended.
Figure 11B:
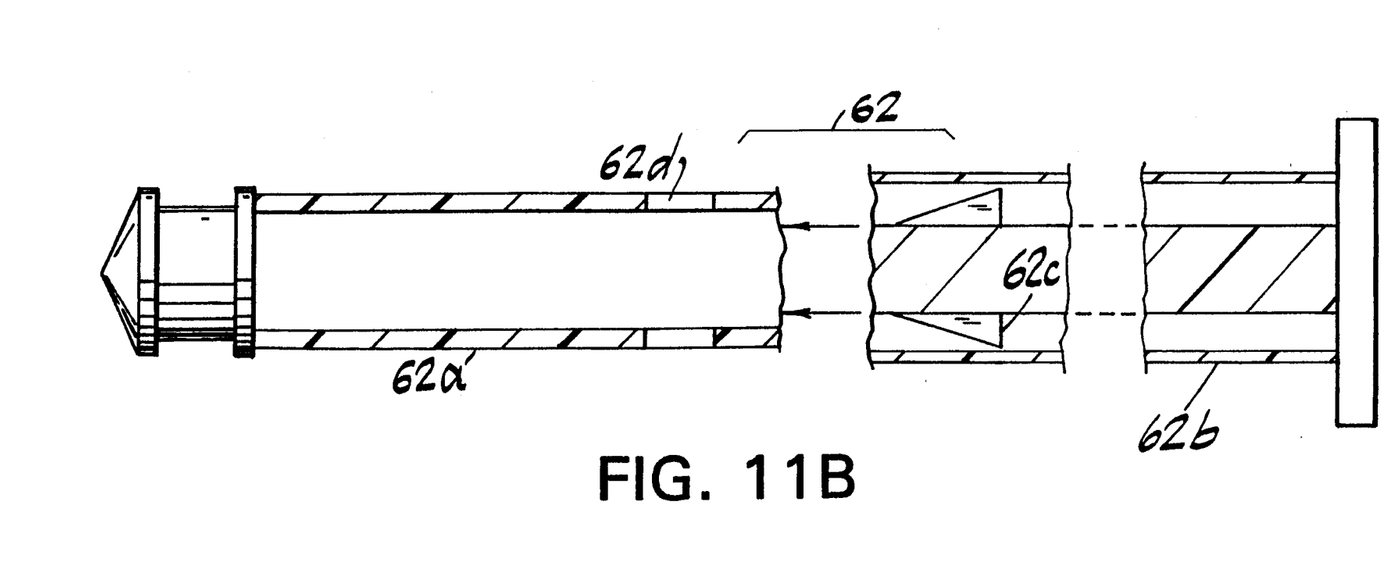
Figure 11D:
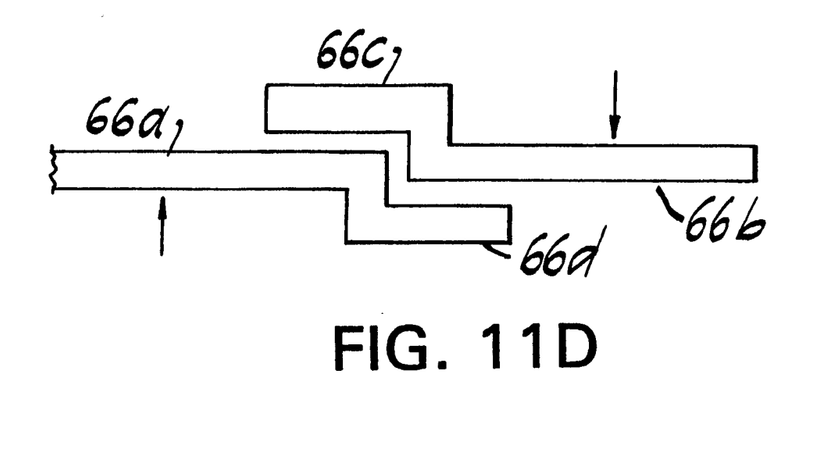

As shown in FIGS. 11A-11D, the improved plunger has two portions which telescope onto each other to provide a shortened length and are extended to a lock-and-detent position to provide its full length. FIG. 11A shows a first version wherein the plunger 60 has a solid portion 60b toward the open end of the syringe which telescopes into a hollow portion 62 at the distal end to a shortened length. When the plunger is to be extended to its full length, the solid portion 60b is pulled back until raised clips 60c on the plunger ribs engage in holes 60d in the hollow portion 60a. FIG. 11B shows another version wherein the plunger 60 has a hollow portion 62b toward the open end of the syringe into which a solid portion 62a at the distal end telescopes. FIG. 11C shows another version in which the plunger 64 has a round shape, a hollow distal-end portion 64a, solid open-end portion 64b, clips 64c, and engagement holes 64d. FIG. 11D shows an alternate engaging means in which the two plunger portions 66a, 66b are telescoped in the shortened position, and locked in the extended position by the spring force holding mutual step shoulder portions 66c, 66d together.

Although the invention has been described with reference to certain preferred embodiments, it will be appreciated that many other variations and modifications thereof may be devised in accordance with the principles disclosed herein. All such described embodiments and variations and modifications thereof are intended to be encompassed within the scope of the invention as defined in the following claims.

What is claimed is:

1. In a disposable safety needle and syringe assembly comprising
   a syringe including a housing having opposing open ends,
   a plunger and plunger piston movably positioned within said housing from one end,
   a needle and needle support positioned at the other end of said housing with said needle including an external portion extending from said housing, and
   a needle shield movably positioned within said housing from said other end, said needle shield being movable from said housing by movement of said plunger and said plunger piston following completion of an injection whereby said needle shield envelopes said needle portion extending from said housing to prevent accidental needle sticks,
   the improvement wherein said syringe housing has detent members provided on inner walls thereof, and said needle shield has engaging points formed thereon for engaging the detent members of said syringe housing to positively lock said needle shield in the positions wherein the needle is not covered and wherein the needle is covered by said needle shield.

2. The disposable safety needle and syringe assembly as defined by claim 1 wherein said needle includes an internal needle portion within said housing, a shield piston around said internal needle portion and abutting said needle shield, said shield piston defining one wall of a fluid cavity within said syringe, said shield piston being engagable by said plunger piston in moving said needle shield from said housing.

3. The disposable safety needle and syringe assembly as defined by claim 2 wherein said plunger includes a central bore for receiving said internal needle portion as said plunger and said plunger piston move said needle shield from said syringe housing.

4. The disposable safety needle and syringe assembly as defined by claim 2 wherein said needle support includes a central portion and a plurality of ribs extending therefrom and engaging an inner surface of said syringe housing, said needle shield including a plurality of segments each positioned between two of said ribs.

5. The disposable safety needle and syringe assembly as defined by claim 4 wherein said needle shield further includes a generally hemispherical end portion supported by said segments outside of said syringe housing, said end portion including a hole through which said needle extends.

6. The disposable safety needle and syringe assembly is defined by claim 5 wherein said syringe housing includes detents on said inner surface, said shield piston and said plunger piston being limited in travel within said syringe housing by said detents.

7. The disposable safety needle and syringe assembly as defined by claim 6 wherein said plunger piston is restricted from retraction from a limit of travel by said detents.

8. The disposable safety needle and syringe assembly as defined by claim 7 wherein said plunger piston is disengagable from said plunger at said limit of travel upon withdrawal of said plunger from said syringe housing.

9. The disposable safety needle and syringe assembly as defined by claim 2 wherein said syringe housing includes detents on said inner surface, said shield piston and said plunger piston being limited in travel within said syringe housing by said detents.

10. The disposable safety needle and syringe assembly as defined by claim 9 wherein said plunger piston is restricted from retraction from a limit of travel by said detents.

11. In a syringe assembly having a syringe including a housing having an open end and a distal end, a plunger and plunger piston movably positioned within said syringe housing from the open end, said plunger having a portion extending from the open end of the syringe housing for injection use thereof, a needle positioned at the distal end with a portion thereof projecting from the syringe housing, and a needle shield movably positioned within the syringe housing at the distal end so as to be movable from said syringe housing by movement of said plunger following an injection use such that the needle shield covers the needle portion extending from the syringe housing to prevent accidental needle sticks,
    the improvement comprising said plunger having an open-end portion and a distal-end portion which telescope one into the other, such that said plunger has a shortened length when said plunger portions are telescoped together and the plunger projecting portion is disposed flush with the open end of the syringe housing to prevent accidental pressing thereof, and said plunger has a longer length when said plunger portions are extended from their telescoped position to allow the plunger projecting portion to project from the open end of the syringe housing for injection use thereof.

12. The improvement for a plunger according to claim 11, wherein said open-end plunger portion is solid and telescopes into a hollow distal-end plunger portion.

13. The improvement for a plunger according to claim 11, wherein said distal-end plunger portion is solid and telescopes into a hollow open-end plunger portion.

14. The improvement for a plunger according to claim 11, wherein said plunger portions have mutually engaging means for locking them together when extended.

* * * * *